United States Patent [19]

Garner

[11] 4,438,034

[45] Mar. 20, 1984

[54] PROCESS FOR PREPARING LACTAM MAGNESIUM HALIDES

[75] Inventor: Albert Y. Garner, Manchester, Mo.

[73] Assignee: Monsanto Company, St. Louis, Mo.

[21] Appl. No.: 456,702

[22] Filed: Jan. 10, 1983

[51] Int. Cl.$^3$ ............................................. C07D 223/10
[52] U.S. Cl. .......................... 260/239.3 R; 260/239 A;
548/543; 546/243
[58] Field of Search ................. 260/239.3 R, 239 AL;
548/543; 546/243

[56] References Cited

U.S. PATENT DOCUMENTS 3,346,566 10/1967 Chiddix et al. .............. 260/239.3 R
3,451,963 6/1969 Tierney et al. .............. 260/239.3 R

OTHER PUBLICATIONS

Ioffe et al., "The Organic Compounds of Magnesium, Beryllium, Calcium, Strontium and Barium" (North Holland Publishing Company), (Amsterdam), pp. 52-53, (1967).

Chemical Abstracts, vol. 83, (1975), Abstract No. 178368, Abstracting Hungarian Teljes 9,419, Feb. 28, 1975.

Primary Examiner—Robert T. Bond
Attorney, Agent, or Firm—Michael C. Schiffer; P. D. Matukaitis; A. H. Cole

[57] ABSTRACT

A method of preparing a lactam magnesium halide comprising the steps of:
a. reactively admixing magnesium, hydrocarbon halide and lactam in the presence of cyclic ether solvent, wherein the halide is either chloride or bromide; and
b. removing the cyclic ether and the hydrocarbon residue.

34 Claims, No Drawings

PROCESS FOR PREPARING LACTAM MAGNESIUM HALIDES

BACKGROUND OF THE INVENTION

The present invention relates to a method of preparing lactam magnesium salt. Specifically, the present invention relates to a method of preparing lactam magnesium halide by reacting together magnesium, a hydrocarbon halide, and lactam monomer.

Generally, lactam magnesium salts are prepared by adding an ether solution of the Grignard reagent to lactam either in a solvent or in molten form. The solvent is then removed along with the resulting hydrocarbon residue leaving a solution of lactam magnesium salt. Typical Grignard reagents utilized in the process of making lactam magnesium salt are alkyl magnesium halides wherein the alkyl is of a low molecular weight (i.e. ethyl).

The major drawback with the above-described method of preparing lactam magnesium salts is the complicated and involved process of first forming the Grignard reagent and then reacting lactam therewith, and secondly, the difficulty in handling lower alkyl Grignards which are highly exothermically reactive with water and are dangerous to transport.

SUMMARY OF THE PRESENT INVENTION

The present invention overcomes the above discussed disadvantages and other deficiencies of the prior art by providing a method of preparing lactam magnesium halide from magnesium, a hydrocarbon halide and lactam monomer wherein the halide is either chloride or bromide.

The present invention involves placing into reactive contact magnesium, a hydrocarbon halide, and lactam monomer, in the presence of a cyclic ether which acts as a solvent. The reaction products are the lactam magnesium halide and a hydrocarbon residue. Removal of both the solvent and the hydrocarbon resideue leaves essentially the lactam magnesium halide.

The present invention allows the preparation of the lactam magnesium halide without the use of highly exothermically reactive lower alkyl Grignards. Furthermore, the present invention allows for the preparation of the lactam magnesium halide in a one step process as compared to first preparing the lower alkyl Grignards which are then mixed with lactam monomer.

DESCRIPTION OF THE PREFERRED EMBODIMENTS

As previously stated, the present invention involves preparation of a lactam magnesium halide. The process of the present invention involves reactively admixing magnesium, a hydrocarbon halide, and lactam in the presence of a cyclic ether. The result is the formation of the lactam magnesium halide and hydrocarbon residue.

The temperature at which the reaction is typically carried out is below that of the boiling point of the particular hydrocarbon halide or halides used. Preferably, this temperature is maintained between about 38° C. and about 80° C.

Hydrocarbon halides useful for the practice of the present invention can be selected from aliphatic or aromatic halides, dihalides, or polyhalides with the halide being either chloride or bromide. Examples of particular halides are ethylbromide, 1,2-dibromoethane, 1,4-dibromo-2-butene, bromobenzene, n-butyl chloride, 1,2-dichloropropane, n-propyl bromide and cyclohexyl bromide. The preferred hydrocarbon halides are the aliphatic and aromatic chloride and bromide species, with the more preferred being the bromide species.

While any lactam is suitable for use in the process of the present invention, preferred lactams are caprolactam and lauryl lactam, more preferably caprolactam.

It should be noted here that the lactam magnesium halide prepared in accordance with the process of the present invention has, as is known in the art, particular utility as an anionic catalyst for nylon or nylon block copolymer polymerization. The use of lactam magnesium halides, particularly caprolactam magnesium chloride as an anionic catalyst for the polymerization of nylon block copolymers, is discussed and illustrated in U.S. Pat. No. 4,031,164 issued to Hedrick et al on June 21, 1977, which is incorporated herein. It should be noted that when lactam magnesium halides are utilized as anionic catalysts for the polymerization of nylon or nylon block copolymers in accordance with the process of the Hedrick et al patent, it is preferable that the lactam used to prepare the lactam magnesium halide be the same lactam which is to be polymerized and even more preferably that the lactam be present in stoichiometic excess during the reaction.

The use of cyclic ether as the solvent for the process of the present invention is critical. It has been found that when preparing lactam magnesium halides in accordance with the present invention a gummy paste believed to comprise the ether and the forming lactam magnesium halide results when using an acyclic ether. Removal of the ether from this gummy paste is difficult. It is theorized that the lactam magnesium halide complexes as it forms with acyclic ethers. It should be noted that this is only a theory and should not be taken in any manner to limt the scope of the present invention. Examples of useful cyclic ethers are dioxane, tetrahydrofuran and tetrahydropyran with the preferred solvent being tetrahydrofuran.

The following Examples illustrate the process of the present invention. These Examples will illustrate this process using various types of hydrocarbon halides and lactams and will also demonstrate the criticality of using a cyclic ether solvent.

EXAMPLES 1 THROUGH 3

PREPARATION OF CAPROLACTAM MAGNESIUM BROMIDE

The following Examples were prepared by reacting caprolactam, ethylbromide, and magnesium in tetrahydrofuran to form caprolactam magnesium bromide.

EXAMPLE 1

A mixture of 93.08 grams (0.824 mole) of caprolactam and 8.45 grams (0.0775 mole) of ethylbromide in 200 milliliters of tetrahydrofuran was dried over anhydrous magnesium sulfate. A small amount of this mixture was added to an oven-dried flask containing 1.885 grams (0.0775 mole) of magnesium turnings and a crystal of iodine. This mixture was then heated and stirred until the ingredients began to react. The remainder of the caprolactam ethylbromide mixture was added to the flask over a one hour period with continuous stirring. The mixture was heated to a slow reflux at 69° C. After all of the solution had been added, the heat was removed and a small amount of ethylbromide was added while continually stirring the mixture. The solution became cloudy and the temperature rose from 35° C. to 45° C. The lactam magnesium bromide began to precipitate out of solution and after 1 ½ hours, the temperature began to fall. At 34° C., a small residue of magnesium still remained in the precipitated caprolactam magnesium bromide. The solution was heated to reflux to finish the reaction. The tetrahyrofuran was removed by first distillation at atmospheric pressures and then removed under vacuum. The remaining hot solution was poured into a polyethylene bag under nitrogen and kneaded until flakes were formed.

A sample of the above prepared caprolactam magnesium bromide was used to catalyze the preparation of nylon block copolymers in accordance with the procedures set forth above in the incorporated by reference Hedrick et al patent.

EXAMPLE 2

A solution of 17 grams (0.156 mole) of ethylbromide and 50 milliliters of tetrahydrofuran was dried over magnesium sulfate. A portion of this solution was added to a slurry of 50 grams (0.442 mole) of topped caprolactam, 3.77 grams (0.155 mole) of magnesium turnings, and a crystal of iodine in 50 milliliters of tetrahydrofuran. This mixture was heated to 50° C. with the reaction between the ingredients confirmed by the observance of a continuous stream of fine bubbles. More of the ethylbromide solution was added at an increasing rate over a 9 minute period. Initially, the temperature of the solution was 49° C. but with vigorous stirring, the temperature rose to 53° C. and a white precipitate began to form. After another 17 minutes, the termperature had reached 60° C. After 1 ½ hours, the temperature dropped back down to 39° C. and external heat was applied to maintain the temperature of the solution at 45° C. After 4 hours, additional ethylbromide and 50 milliliters of tetrahydrofuran were added to speed up the reaction. After all of the magnesium had disappeared, 136 grams (1.2 miles) of molten, topped caprolactam were added to the solution. The tetrahydrofuran was removed by first distillation and then under vacuum. The solution was then poured under nitrogen into a polyethylene bag for flaking.

EXAMPLE 3

A solution of 20 grams (0.184 mole) of ethylbromide and 25 milliliters of tetrahydrofuran was dried over magnesium sulfate. A portion of this ethylbromide solution was added to a mixture of 20 grams (0.177 mole) of topped caprolactam, 3.77 grams (0.155 mole) of magnesium turnings, and 25 milliliters of tetrahydrofuran. The reaction was initiated without heating at 40° C. The temperature of the mixture rose to 64° C. with solvent refluxing. The remainder of the ethylbromide solution was added over a 72 minute period while maintaining the temperature below 50° C. A white precipitate began to form early in reaction but went back into solution towards the end. All of the magnesium disappeared in 1 ½ hours. The mixture was then refluxed for ten minutes to insure complete reaction due to the cloudiness of the solution. Twenty-five milliliters of tetrahydrofuran were added to wash down the walls of the flask. The mixture was then cooled and a solid white precipitate fell out of solution. One hundred fifty-six grams (1.47 moles) of topped caprolactam was then added to the solution under nitrogen. The tetrahydrofuran was removed by first distillation and then under vacuum. The remaining solution was cooled to 85° and poured under nitrogen into a double polyethylene bag and sealed. This bag was kneaded as cooling continued so as to form small particle flakes. The weight of the sample was 190.7 grams. A portion of this material was then utilized to catalyze the formation of nylon block copolymer as discussed in Example 1.

EXAMPLES 4 AND 5

The following Examples illustrate the preparation of lactam magnesium halide using an acyclic ether. This demonstrates that the preparation of lactam magnesium halide using acyclic ether increases the potential of forming a gummy paste, which is believed to comprise the ether and the forming product, from which removal of the ether is difficult.

EXAMPLE 4

In this Example, the solvent used was diethyl ether.

A solution of 37.05 grams (0.34 mole) of ethyl bromide in 25 milliliters of diethyl ether was added in portions to a slurry of 36.2 grams (0.32 mole) of caprolactam, magnesium turnings, and a crystal of iodine in 50 milliliters of diethyl ether. The reaction was started with a slight warming of the solution. As the reaction proceeded, the product began to precipitate out and a gummy paste began forming as the volume of the diethyl ether solvent decreased. It is believed that the diethyl ether complexed with the forming product. More diethyl ether was added to keep the mixture fluid. When all of the bromide solution had been added, the stirrer was stopped as the product had a putty-like consistency which tended to ball up. The mixture was refluxed for an hour and cooled to room temperature and scraped out of the flask under nitrogren into a polyethylene bag. This bag was placed into a dessicator which was evacuated and pumped to remove occluded solvent. The weight of the final product was 70.1 grams. This material was then used to catalyze the formation of nylon block copolymers as discussed above in Example 1.

EXAMPLE 5

In this Example, a mixture of cyclohexane and tetrahydrofuran was used as a solvent.

A solution of 37.05 grams (0.34 mole) of ethylbromide in 25 milliliters of dry cyclohexane was added to a slurry of 36.2 grams (0.32 mole) of caprolactam, 7.45 grams (0.31 mole) of magnesium turnings, and a crystal of iodine in a mixture of 27.6 milliliters of tetrahydrofuran and 22.4 milliliters of cyclohexane. Upon heating and rapid stirring of the mixture the reaction began. The temperature rose to over 66° C. and the mixture turned white as a solid product precipitated. The remainder of the ethylbromide solution was added at a rate to keep the temperature between 55 and 60° C. The precipitate began to ballup as more of it was formed. When the temperature dropped to 45° C., 50 milliliters of cyclohexane were added in an attempt to keep the precipitate from aggregating. The mixture was then heated to 47° C. to allow the remaining magnesium caught up in the precipitate mass to react. When all of the magnesium had disappeared, 30 milliliters of tetrahydrofuran were added to facilitate the breaking up of the precipitate. The solid precipitate was filtered under nitrogen and washed with cyclohexane and placed under vacuum in a dessicator for 72 hours in an effort to remove the remaining solvent after which time it still appeared that the precipitate contained some solvent. The weight of the final precipitate was 78.34 grams. This material was also used to catalyze the preparation of nylon block copolymers as discussed above in Example 1.

EXAMPLES 6 THROUGH 8

The following Examples demonstrate the preparation of caprolactam magnesium bromide from difunctional hydrocarbon bromides and aromatic hydrocarbon bromides.

EXAMPLE 6

A solution of 8 grams (0.043 mole) of ethylene dibromide in 10 milliliters of tetrahydrofuran was dried over magnesium sulfate. A portion of this dibromide solution was added to a slurry of 9.04 grams (0.08 mole) of caprolactam, 1.89 grams (0.078 mole) of magnesium turnings, and a crystal of iodine in 30 milliliters of tetrahydrofuran. The resulting mixture was heated to 40° C. and vigorously stirred. The iodine color disappeared and the temperature dropped back down to 35° C. At this time the remainder of the dibromide solution was added. The mixture frothed as the temperature rose to 60° C. with the refluxing of the tetrahydrofuran. The solution was then cooled and maintained at a temperature of 40° C. and after three hours, the solution was allowed to cool further. This solution was then filtered and air dried leaving 0.99 grams of unreated magnesium which indicates that only a small amount of lactam magnesium bromide was formed due to the competing reaction between the hydrocarbon dibromide and magnesium to give olefin and magnesium bromide.

EXAMPLE 7

A solution of 12.4 grams (0.058 mole) of 1,4-dibromo-2-butene in 25 milliliters of tetrahydrofuran was dried. A portion of the solution was added to a mixture of 14 grams (0.124 mole) of caprolactam and 2.8 grams (0.116 mole) of magnesium in 25 milliliters of tetrahydrofuran. As a reaction started, a white precipitate began to form. When the rest of the bromide solution was added, the mixture turned charcoal gray. External heat was used to keep the mixture at 65° C. for 3 ½ hours. The mixture was stirred overnight. A large amount of magnesium remained. Methanol was added to the reaction mixture to quench the reaction. 1.26 grams of magnesium were recovered, thus indicating again that there was a competing reaction as discussed in Example 6.

EXAMPLE 8

A solution of 3.4 grams (0.34 mole) of bromobenzene in 25 milliliters of tetrahydrofuran was dried. A portion of this solution was added to a slurry of 36.2 grams (0.32 mole) of caprolactam, 7.54 grams (0.31 mole) of magnesium turnings and a crystal of iodine in 50 milliliters of tetrahydrofuran. This mixture was warmed to 40° C. with rapid stirring. The remainder of the bromobenzene solution was added over a two hour span. The mixture turned gray-white and was heated to reflux at 73° C. to insure the reaction of all the magnesium. When all the magnesium had disappeared, the slurry was allowed to cool to 27° C. The flask was then chilled in ice water to precipitate as much of the product as possible. The solid was filtered under nitrogen, producing a white solid which was placed in a weighed polyethylene bag. The bag was placed under vacuum in a dessicator and pumped dry for two hours. The dried sample weighed 58.75 grams which indicated that 87.7% of the product was recovered. Water and methanol were added to the filterate causing a warming and cloudiness, thus indicating the presence of more lactam magnesium bromide. A sample of the formed product was used to catalyze nylon block copolymers in accordance with procedures stated above for Example 1.

EXAMPLES 9 AND 10

The following Examples demonstrate the use of hydrocarbon chlorides in forming lactam magnesium halides.

EXAMPLE 9

A solution of 17 grams (0.184 mole) of n-butyl chloride in 25 milliliters of diethyl ether was dried and then added to a slurry of 3.77 grams (0.155 mole) of magnesium turnings, 20 grams (0.177 mole) of topped caprolactam and a crystal of iodide in 50 milliliters of diethyl ether. The reaction started slowly with heating and vigorous stirring. After 7 hours of refluxing, all of the magnesium had disappeared and a white slurry formed. The mixture was sealed under nitrogen for 64 hours; 166 grams (1.47 moles) of caprolactam were then added to the mixture. The solvent was removed first by distillation and then by vacuum. The final clear solution was poured under nitrogen into a polyethylene bag at 90° C. As it cooled, it was kneaded to prevent lump formation of the product. The final weight of the product was 109.6 grams. A sample of this material was used to catalyze the formation of nylon block copolymers in accordance with the procedures stated above in Example 1.

EXAMPLE 10

A solution of 13.13 grams (0.116 mole) of 1,2-dichloropropane in 25 milliliters of tetrahydrofuran was dried and added to a slurry of 20.0 grams (0.177 mole) of topped caprolactam, 3.77 grams (0.155 mole) of magnesium and a crystal of iodine in 25 milliliters of tetrahydrofuran. The mixture was heated to 75° C. but the reaction did not start. The addition of a milliliter of ethylbromide solution in tetrahydrofuran started the reaction which boiled and refluxed without external heating. After the reaction had subsided, the temperature was maintained at 45° C. by heating for 22 hours. The reactive mixture was quenched with methanol and water and 1 gram of unreacted magnesium was recovered.

EXAMPLE 11

The following Example demonstrates the use of a lactam other than caprolactam in preparing lactam magnesium halide.

EXAMPLE 11

A solution of 20 grams (0.184 mole) of ethylbromide in 25 milliliters of tetrahydrofuran was dried and a portion was added to a slurry of 34.87 grams (0.177 mole) of lauryl lactam that had been vacuum dried overnight at 90° C., 3.77 grams (0.155 mole) of magnesium turnings and a crystal of iodine in 50 milliliters of tetrahydrofuran at 25° C. A third of this bromide solution was added to the mixture with rapid stirring. As the reaction started, the temperature rose to 57° C. The remainder of the bromide solution was then added over a one hour period. As temperature receded to 41° C., all of the lauryl lactam and most of the magnesium went into solution. External heating was used to maintain the temperature at 47° C. After 40 minutes, all of the magnesium had disappeared. An additional 164.2 grams (0.83 mole) of dry lauryl lactam was added to the mixture while stirring and heating were maintained. After thorough mixing for one hour, the solvent was removed by distillation and the temperature was raised to 172° C. to complete the reaction. The hot solution was cooled to 165° C. and was then poured into a hot oven-dried glass bottle. The material solidified as it cooled. The final weight of the material was 191.82 grams. A sample of this material was used to catalyze nylon block copolymer preparation in accordance with the procedures laid out in Example 1.

From the above Examples, it can be seen that the use of cyclic ether minimizes the potential of preparing a gummy paste, believed to comprise ether and the forming lactam magnesium halide, from which the removal of the ether is difficult. This is specifically seen by comparing Examples 1 through 3, wherein the tetrahydrofuran was easily removed, with Examples 4 and 5 wherein the amount of the ether diminished as the reaction proceeded with the resulting material being in the form of a gummy paste believed to be the diethyl ether complexed with the forming lactam magnesium halide precipitate. This easy removal of the solvent is especially critical when the lactam magnesium halide is to be used to catalyze nylon or nylon block copolymers. If any solvent remains, it creates the potential of bubbling during the preparation of molded products from the nylons or nylon block copolymers which would create imperfections in the final molded product.

In general, when lactam magnesium halides are prepared using hydrocarbon halides in accordance with the process of the present invention, equal mole amounts of the lactam, magnesium and hydrocarbon halide can be used. When a hydrocarbon dihalide is used in accordance with the process of the present invention, it may be possible to use a half mole amount of the dihalide since theoretically each halide should react independently. However, as seen from the above Examples 6 and 7, there is the potential for a competing reaction between hydrocarbon dihalides and magnesium. Thus, it is preferable to use the dihalides in at least equal mole amounts to the lactam and magnesium.

As stated previously, it is preferable to use excess lactam in varying amounts depending upon the desired ratio of lactam magnesium halide to lactam after removal of the hydrocarbon and ether. As the above Examples demonstrate, it is preferable to add the lactam and magnesium to the cyclic ether first and then over a period of time add the hydrocarbon halide. This allows a means of controlling the reaction and the resulting increase in temperature which as stated above should not exceed the boiling point of the hydrocarbon halide which is being used. Mixing by any known means during the addition of the hydrocarbon halide enhances the reaction.

As seen from the above Examples, the mole amount of the cyclic ether used is not critical for the reaction but should be in a sufficient amount to allow for the ingredients to come into reactive contact. Preferably, enough ether should be used to allow for the preparation of a saturated solution of lactam in ether. While not detrimental to the process of the present invention, an excess amount of cyclic ether would require additional time for removal. This removal of the ether can be carried out by any well known means in the art for removing solvent, such as, by suction under nitrogen, pressure filtration or gravity filtration. The hydrocarbon residue formed during the process of the present invention will typically evaporate off during the reaction, but if necessary can be removed by any known means such as those discussed for solvent removal.

As seen in the above Examples, the magnesium, while not going into the solution with the ether, gradually disappears as the halide is added due to reaction occurring. This allows a visual means to check the progress of the reaction and especially when a hydrocarbon halide is used, the complete disappearance of magnesium indicates that the reaction is completed.

While the preferred embodiments have been described and illustrated, various modifications may be made thereto without the departing from the spirt and scope of the invention. Accordingly, it is to be understood that the present invention has been described by way of illustration and not limitation.

What is claimed:

1. A method of preparing a lactam magnesium halide comprising the steps of:
   a. Reactively admixing magnesium, hydrocarbon halide, and lactam in the presence of a cyclic ether solvent, wherein the halide is either chloride or bromide; and
   b. removing the cyclic ether and the hydrocarbon residue.

2. The method of claim 1 wherein the cyclic ether is tetrahydrofuran.

3. The method of claim 1 wherein said lactam is caprolactam.

4. The method of claim 2 wherein said lactam is caprolactam.

5. The method of claim 1 wherein the hydrocarbon halide is selected from the group consisting of aliphatic halides, aliphatic dihalides, aliphatic polyhalides, aromatic halides, aromatic dihalides, and aromatic polyhalides.

6. The method of claim 2 wherein the hydrocarbon halide is selected from the group consisting of aliphatic halides, aliphatic dihalides, aliphatic polyhalides, aromatic halides, aromatic dihalides, and aromatic polyhalides.

7. The method of claim 4 wherein the hydrocarbon halide is selected from the group consisting of aliphatic halides, aliphatic dihalides, aliphatic polyhalides, aromatic halides, aromatic dihalides, and aromatic polyhalides.

8. The method of claim 5 wherein the hydrocarbon halide is an aliphatic halide or aromatic halide.

9. The method of claim 6 wherein the hydrocarbon halide is an aliphatic halide or aromatic halide.

10. The method of claim 7 wherein the hydrocarbon halide is an aliphatic halide or aromatic halide.

11. The method of claim 2 wherein the halide of the hydrocarbon halide is bromide.

12. The method of claim 6 wherein the halide of the hydrocarbon halide is bromide.

13. The method of claim 8 wherein the halide of the hydrocarbon is bromide.

14. The method of claim 9 wherein the halide of the hydrocarbon halide is bromide.

15. The method of claim 10 wherein the halide of the hydrocarbon halide is bromide.

16. The method of claim 1 wherein said lactam is in stoichiometric excess.

17. The method of claim 2 wherein said lactam is in stoichiometric excess.

18. The method of claim 4 wherein said lactam is in stoichiometric excess.

19. The method of claim 6 wherein said lactam is in stoichiometric excess.

20. The method of claim 8 wherein said lactam is in stoichiometric excess.

21. The method of claim 9 wherein said lactam is in stoichiometric excess.

22. The method of claim 10 wherein said lactam is in stoichiometric excess.

23. The method of claim 13 wherein said lactam is in stoichiometric excess.

24. The method of claim 14 wherein said lactam is in stoichiometric excess.

25. The method of claim 15 wherein said lactam is in stoichiometric excess.

26. The method of claim 1 wherein the reactively admixing is carried out at a temperature below the boiling point of the hydrocarbon halide.

27. The method of claim 2 wherein the reactively admixing is carried out at a temperature below the boiling point of the hydrocarbon halide.

28. The method of claim 4 wherein the reactively admixing is carried out at a temperature below the boiling point of the hydrocarbon halide.

29. The method of claim 7 wherein the reactively admixing is carried out at a temperature below the boiling point of the hydrocarbon halide.

30. The method of claim 10 wherein the reactively admixing is carried out at a temperature below the boiling point of the hydrocarbon halide.

31. The method of claim 15 wherein the reactively admixing is carried out at a temperature below the boiling point of they hydrocarbon halide.

32. The method of claim 17 wherein the reactively admixing is carried out at a temperature below the boiling point of the hydrocarbon halide.

33. The method of claim 22 wherein the reactively admixing is carried out at a temperature below the boiling point of the hydrocarbon halide.

34. The method of claim 25 wherein the reactively admixing is carried out at a temperature below the boiling point of the hydrocarbon halide.

* * * * *